(12) United States Patent
Jing et al.

(10) Patent No.: US 11,795,473 B2
(45) Date of Patent: Oct. 24, 2023

(54) USE OF TONICIFYING AGENTS TO ENHANCE RECOMBINANT ADENO-ASSOCIATED VIRUS YIELD

(71) Applicant: Ultragenyx Pharmaceutical Inc., Novato, CA (US)

(72) Inventors: Ying Jing, Reinach (CH); Jan Panteli, Cambridge, MA (US)

(73) Assignee: Ultragenyx Pharmaceutical Inc., Novato, CA (US)

( * ) Notice: Subject to any disclaimer, the term of this patent is extended or adjusted under 35 U.S.C. 154(b) by 1059 days.

(21) Appl. No.: 16/340,758

(22) PCT Filed: Oct. 13, 2017

(86) PCT No.: PCT/US2017/056588
§ 371 (c)(1),
(2) Date: Apr. 10, 2019

(87) PCT Pub. No.: WO2018/071817
PCT Pub. Date: Apr. 19, 2018

(65) Prior Publication Data
US 2021/0277416 A1 Sep. 9, 2021

Related U.S. Application Data

(60) Provisional application No. 62/408,420, filed on Oct. 14, 2016.

(51) Int. Cl.
*C12N 15/86* (2006.01)
*C12N 7/00* (2006.01)

(52) U.S. Cl.
CPC .............. *C12N 15/86* (2013.01); *C12N 7/00* (2013.01); *C12N 2750/14152* (2013.01)

(58) Field of Classification Search
None
See application file for complete search history.

(56) References Cited

U.S. PATENT DOCUMENTS

| | | | |
|---|---|---|---|
| 5,387,484 A | 2/1995 | Doany et al. | |
| 5,658,785 A | 8/1997 | Johnson | |
| 5,688,676 A | 11/1997 | Zhou et al. | |
| 5,691,176 A | 11/1997 | Lebkowski et al. | |
| 5,741,683 A | 4/1998 | Zhou et al. | |
| 5,872,005 A | 2/1999 | Wang et al. | |
| 6,004,797 A | 12/1999 | Colosi | |
| 6,127,175 A | 10/2000 | Vigne et al. | |
| 6,156,303 A | 12/2000 | Russell et al. | |
| 6,489,162 B1 | 12/2002 | Shenk et al. | |
| 6,566,118 B1 | 5/2003 | Atkinson et al. | |
| 6,723,551 B2 | 4/2004 | Kotin et al. | |
| 6,753,419 B1 | 6/2004 | Toniatti et al. | |
| 6,846,665 B1 | 1/2005 | Horer et al. | |
| 6,943,019 B2 | 9/2005 | Wilson et al. | |
| 7,271,002 B2 | 9/2007 | Kotin et al. | |
| 7,510,872 B2 | 3/2009 | Clark et al. | |
| 8,163,543 B2 | 4/2012 | Urabe et al. | |
| 8,409,842 B2 | 4/2013 | Clark et al. | |
| 8,512,981 B2 | 8/2013 | Hermens et al. | |
| 8,980,247 B2 | 3/2015 | Meyers et al. | |
| 2002/0081721 A1 | 6/2002 | Allen et al. | |
| 2002/0115189 A1 | 8/2002 | Natsoulis et al. | |
| 2002/0127582 A1 | 9/2002 | Atkinson et al. | |
| 2004/0235173 A1 | 11/2004 | Bleck et al. | |
| 2005/0112765 A1 | 5/2005 | Li et al. | |
| 2005/0148076 A1 | 7/2005 | Allen | |
| 2006/0013063 A1 | 1/2006 | Singh | |
| 2010/0248355 A1 | 9/2010 | Atkinson et al. | |
| 2011/0251547 A1 | 10/2011 | Xing et al. | |
| 2012/0058917 A1 | 3/2012 | Gaken et al. | |
| 2014/0004568 A1* | 1/2014 | Shen ....................... | C12N 7/00 435/235.1 |
| 2014/0056919 A1 | 2/2014 | Xing et al. | |
| 2014/0359799 A1 | 12/2014 | Wang et al. | |
| 2015/0024467 A1 | 1/2015 | Sheldon et al. | |
| 2015/0353899 A1 | 12/2015 | Pechan et al. | |

FOREIGN PATENT DOCUMENTS

| | | |
|---|---|---|
| WO | WO-1996/17947 A1 | 6/1996 |
| WO | WO-2000/14205 A2 | 3/2000 |
| WO | WO-2000/24916 A1 | 5/2000 |
| WO | WO-2000/47757 A1 | 8/2000 |
| WO | WO-2012/122625 A1 | 9/2012 |

OTHER PUBLICATIONS

Clark et al., "Cell lines for the production of recombinant adeno-associated virus", Human Gene Therapy. vol. 6, (1995), pp. 1329-1341.
Hermonat et al., "Human papillomavirus type 16 helper functions for adeno-associated virus type 2 replication", Molecular therapy. vol. 9,(2004), S289-290.
International Search Report and Written Opinion for corresponding International Application No. PCT/US2017/056588 dated Feb. 22, 2018.
Martin et al., "Generation and Characterization of Adeno-Associated Virus Producer Cell Lines for Research and Preclinical Vector Production", Human Gene Therapy Methods. vol. 24, (2013), pp. 253-269.
Strobel et al., "Comparative Analysis of Cesium Chloride- and Iodixanol-Based Purification of Recombinant Adeno-Associated Viral Vectors for Preclinical Applications", Human Gene Therapy Methods. vol. 26, No. 4, (2015), pp. 147-157).

(Continued)

*Primary Examiner* — Allison M Fox
*Assistant Examiner* — Kimberly A Aron
(74) *Attorney, Agent, or Firm* — Goodwin Procter LLP (57) ABSTRACT

The invention provides methods for the production of recombinant adeno-associated virus vectors (rAAV), comprising culturing producer cells in media with increased osmolality. Also provided are methods for decreasing the production of helper virus by a rAAV producer cell, comprising culturing the producer cell in media with increased osmolality.

17 Claims, 2 Drawing Sheets

(56) References Cited

OTHER PUBLICATIONS

Thorne et al., "Manufacturing recombinant adeno-associated viral vectors from producer cell clones", Human Gene Therapy. vol. 20, (2009), pp. 707-714.
Virag et al., "Producing Recombinant Adeno-Associated Virus in Foster Cells: Overcoming Production Limitations Using a Baculovirus-Insect Cell Expression Strategy", Human Gene Therapy. vol. 20, No. 8 (2009), pp. 807-817.
Wang et al., "Identification of an adeno-associated virus binding epitope for AVB sepharose affinity resin", Molecular Therapy—Methods and Clinical Development. vol. 2, (2015), pp. 1-6.
Weinbauer et al., "Enhanced viral production and infection of bacterioplankton during an iron-induced phytoplankton bloom in the Southern Ocean", Limnology and Oceanography, vol. 54, No. 3, (2009), pp. 774-784.
Williams, "Enhancement of adenovirus plaque formation on HeLa cells by magnesium chloride", Journal of General Virology, vol. 9, No. 3, (1970), pp. 251-255.
Wright, "Review: Transient Transfection Methods for Clinical Adeno-Associated Viral Vector Production", Human Gene Therapy. vol. 20, (2009), pp. 698-706.
Yang et al., "Fatty acid synthase is up-regulated during hepatitis c virus infection and regulates hepatitis c virus entry and production", Hepatology. vol. 48, No. 5, (2008), pp. 1396-1403.
Zhen et al., "Infectious titer assay for adeno-associated virus vectors with sensitivity sufficient to detect single infectious events", Human Gene Therapy. vol. 15, (2004), pp. 709-715.

\* cited by examiner

USE OF TONICIFYING AGENTS TO ENHANCE RECOMBINANT ADENO-ASSOCIATED VIRUS YIELD

CROSS REFERENCE TO RELATED APPLICATION

This application is a U.S. national stage application, filed under 35 U.S.C. § 371, of International Application No. PCT/US2017/056588 filed on Oct. 13, 2017, which claims priority to and the benefit of U.S. Provisional Patent Application No. 62/408,420, filed on Oct. 14, 2016, the entire contents of each of which are incorporated by reference herein for all purposes.

FIELD OF THE INVENTION

The invention relates generally to methods for enhancing recombinant adeno-associated virus vector (rAAV) yield, and, more particularly, the invention relates to the use of tonicifying agents to enhance rAAV yield.

BACKGROUND

Adeno-associated virus (AAV) is a non-pathogenic, replication-defective parvovirus. Recombinant AAV vectors (rAAV) have many unique features that make them attractive as vectors for gene therapy. In particular, rAAV vectors can deliver therapeutic genes to dividing and nondividing cells, and these genes can persist for extended periods without integrating into the genome of the targeted cell. Given the widespread therapeutic applications of rAAV, there exists an ongoing need for improved methods of rAAV vector production including methods to achieve high-titer rAAV vector yields. Previous attempts to improve the production of a variety of viral vectors have included the use of cell culture additives such as metals, trace supplements, salts, and others (See, e.g., Williams, J. Gen. Virol., 9(3): 251-5 (1970), Weinbauer et al., Limnology and Oceanography, 54(3): 774-784 (2009), Yang et al., Hepatology, 48(5): 1396-403 (2008), and U.S. Publication No. 20150353899). rAAV are often produced by means of a helper virus, such as adenovirus (AV). However, any helper virus is a contaminant that must be removed before the rAAV can be used in therapeutic applications. There is therefore also a need in the art to produce rAAV with as little contaminating helper virus as possible.

SUMMARY OF THE INVENTION

The invention is based, in part, upon the discovery that a host cell used in the production of recombinant adeno-associated virus vectors (rAAV) will produce increased amounts of rAAV and decreased amounts of helper virus when the osmolality of the cell culture media is increased via the addition of an ionic tonicifying agent, such as NaCl. The invention is also based, in part, on the discovery that a host cell used in the production of rAAV will produce decreased amount of helper virus when the osmolality of the cell culture media is increased via the addition of a non-ionic tonicifying agent such as sucrose. In one aspect, the invention provides a method for producing a rAAV comprising incubating a host cell in a culture media with increase osmolality. In another aspect, the invention provides a method for decreasing the amount of helper virus produced by a rAAV-producing host cell, comprising incubating the rAAV-producing host cell in cell culture media with increased osmolality due to supplementation with a non-ionic tonicifying agent such as sucrose. In another aspect, the invention provides a method for increasing the production of rAAV and decreasing the production of helper virus produced by a host cell, comprising incubating the host cell in cell culture media with increased osmolality due to supplementation with an ionic tonicifying agent such as NaCl. In yet another aspect, the invention relates to cell culture systems comprising a host cell capable of producing both rAAV and helper virus, and a cell culture media with increased osmolality due to supplementation with a tonicifying agent.

In one aspect of the invention, the tonicifying agent is ionic. It is contemplated that the tonicifying agent may be any ionic tonicifying agent compatible with mammalian or insect cell culture media. Exemplary ionic tonicifying agents include NaCl, KCl, $NaNO_3$, $NaHCO_3$, $Na_2SO_4$, $Na_2HPO_4$, $NaH_2PO_4$, $NaNO_3$, $KNO_3$, $K_2SO_4$, $K_2HPO_4$, $KH_2PO_4$, or $KNO_3$. In one embodiment, the tonicifying agent is NaCl. It is contemplated that, where the tonicifying agent is NaCl, it may be present at a concentration of at least 4.5 g/L (77.0 mM). It is further contemplated that NaCl may be present at a concentration of at least 6.5 g/L (111.2 mM), or at least 7.5 g/L (128.3 mM). It will be understood that other ionic tonicifying agents can be substituted for NaCl by substituting an equal osmolar amount of the alternative salt.

In another aspect of the invention, the tonicifying agent is non-ionic. It is contemplated that the tonicifying agent may be any non-ionic tonicifying agent compatible with mammalian or insect cell culture media. For example, the non-ionic tonicifying agents may be a sugar, including disaccharides and monosaccharides, such as sucrose, fructose, glucose, galactose, mannose, maltose, and trehalose. In one embodiment, the tonicifying agent is sucrose. It is contemplated that, where the tonicifying agent is sucrose, it may be present at a concentration of at least 6.8 g/L (19.9 mM). It is further contemplated that sucrose may be present at a concentration of at least 13.7 g/L (40.0 mM), 29.4 g/L (85.9 mM), or 41.1 g/L (120.0 mM). It will be understood that other non-ionic tonicifying agents can be substituted for sucrose by substituting an equal molar amount of the alternative non-ionic tonicifying agent.

It is contemplated that the osmolality of the culture media, when measured at the start of incubation of the host cell, will be 360 mOsm/kg or higher, 375 mOsm/kg or higher, or 400 mOsm/kg or higher. In one embodiment, the osmolality of the culture medium is sufficient to produce at least a 20% reduction in total helper virus production, relative to that produced by a host cell in a cell culture medium at 266 mOsm/kg. It is further contemplated that the reduction in total helper virus production may be 30%, 40%, or 50%. In another embodiment, the concentration of ionic tonicifying agent is sufficient to produce at least a 50% increase in total rAAV production, relative to that produced by a host cell in a cell culture medium at 266 mOsm/kg. It is further contemplated that the increase in total rAAV production may be 100%, 150%, or 200%. In one embodiment, the period of time the host cell incubated in the cell culture medium with increased osmolality is for at least 2 days. It is further contemplated that the incubation may be at least 3 days or about 4 days.

It is contemplated that the host cell may be a mammalian cell, for example, a HeLa, HEK293, COS, A549, BHK, or Vero cell. It is also contemplated that the host cell may be an insect cell, for example, a Sf9, Sf-21, Tn-368, or BTI-Tn-5B1-4 (High-Five) cell. In one embodiment, the host cell is a HeLa cell. It is contemplated that the host cell may comprise a heterologous nucleotide sequence flanked by AAV inverted terminal repeats, rep and cap genes, or helper virus genes. In one embodiment, the host cell comprises a heterologous nucleotide sequence flanked by AAV inverted terminal repeats, rep and cap genes, and helper virus genes. In one embodiment, the host cell comprises one or more AAV genes stably integrated into the host cell's genome.

It is contemplated that the helper virus may be any virus capable of allowing AAV contained in a host cell to enter the infections phase, for example adenovirus, herpes simplex virus, papilloma virus, or baculovirus. In one embodiment, the helper virus is adenovirus subtype 5 (Ad5).

In certain embodiments, the host cell will be capable of producing both rAAV and helper virus. A host cell is capable of producing rAAV or AV if, in the absence of intervention and given appropriate culture conditions, the cell will produce viral particles, whether or not the particles are released into the cell culture media. A host cell may be capable of producing a virus because it was infected by a live virus, or because it was transfected with viral genes that may exist in the cell transiently, for example, on a plasmid or other extrachromosomal body, or be permanently integrated into the host cell genome. It is contemplated host cells transiently transfected with one or more plasmids containing AAV inverted terminal repeats, rep and cap genes, and infected by live helper virus may be considered capable of producing both rAAV and helper virus. It is further contemplated that host cells containing AAV inverted terminal repeats, rep and cap genes integrated in the host cell's chromosomes and infected with a live helper virus will be considered capable of producing both rAAV and helper virus.

In other embodiments, the host cell is inoculated with non-replicating helper virus. In this situation, the host cell is capable of producing rAAV but not capable of producing helper virus, and thus the beneficial effects of increased osmolality on helper virus production will not occur, however the beneficial effect of increased rAAV production will still be realized.

In other aspects, the invention provides a rAAV produced by any of the contemplated methods, a composition comprising a rAAV produced by any of the contemplated methods, or a cell culture system comprising a host cell capable of producing both rAAV and helper virus and cell culture media with an osmolality of 360 mOsm/kg or higher.

These and other aspects and features of the invention are described in the following detailed description and claims.

BRIEF DESCRIPTION OF THE DRAWINGS

The foregoing and other objects, features and advantages of the invention will become apparent from the following description of preferred embodiments, as illustrated in the accompanying drawings. Like referenced elements identify common features in the corresponding drawings.

DETAILED DESCRIPTION

The invention is based, in part, upon the discovery that the production of rAAV and helper virus in a host cell can be optimized by increasing the osmolality of the culture media through the use of a tonicifying agent, such as NaCl or sucrose. In one aspect, the invention provides a method for producing rAAV using a helper virus, the method comprising incubating a host cell capable of producing both rAAV and helper virus in a cell culture medium containing one or more tonicifying agents and having an osmolality of 360 mOsm/kg or higher at the start of the incubation period. In another aspect, the invention provides a method for decreasing the amount of helper virus produced during the production of rAAV by incubating a host cell in a cell culture medium containing one or more tonicifying agents and having an osmolality of 360 mOsm/kg or higher at the start of the incubation period. In yet another aspect, the invention provides a method for increasing the amount of rAAV produced by a host cell while simultaneously decreasing the amount of helper virus produced by a host cell, by incubating a host cell in a cell culture medium containing one or more tonicifying agents and having an osmolality of 360 mOsm/kg or higher at the start of the incubation period.

1. Adeno-Associated Virus

Adeno-associated virus (AAV) is a small, nonenveloped icosahedral virus of the genus Dependoparvovirus and family Parvovirus. AAV has a single-stranded linear DNA genome of approximately 4.7 kb. AAV includes numerous serologically distinguishable types including serotypes AAV-1 to AAV-12, as well as more than 100 serotypes from nonhuman primates (See, e.g., Srivastava, J. Cell Biochem., 105(1): 17-24 (2008), and Gao et al., J. Virol., 78(12), 6381-6388 (2004)). Any AAV type may be used in the methods of the present invention. AAV is capable of infecting both dividing and quiescent cells of several tissue types, with different AAV serotypes exhibiting different tissue tropism. AAV is non-autonomously replicating, and has a life cycle with a latent phase and an infectious phase. In the latent phase, after a cell is infected with an AAV, the AAV site-specifically integrates into the host's genome as a provirus. The infectious phase does not occur unless the cell is also infected with a helper virus (for example, adenovirus (AV) or herpes simplex virus (HSV)), which allows the AAV to replicate.

The wild-type AAV genome contains two 145 nucleotide inverted terminal repeats (ITRs), which contain signal sequences directing AAV replication, genome encapsidation and integration. In addition to the ITRs, three AAV promoters, p5, p19, and p40, drive expression of two open reading frames encoding rep and cap genes. Two rep promoters, coupled with differential splicing of the single AAV intron, result in the production of four rep proteins (Rep 78, Rep 68, Rep 52, and Rep 40) from the rep gene. Rep proteins are responsible for genomic replication. The Cap gene is expressed from the p40 promoter, and encodes three capsid proteins (VP1, VP2, and VP3) which are splice variants of the cap gene. These proteins form the capsid of the AAV particle.

Because the cis-acting signals for replication, encapsidation, and integration are contained within the ITRs, some or all of the 4.3 kb internal genome may be replaced with foreign DNA, for example, an expression cassette for an exogenous protein of interest. In this case the rep and cap proteins are provided in trans on, for example, a plasmid. In order to produce an AAV vector, a host cell line permissive of AAV replication must express the rep and cap genes, the ITR-flanked expression cassette, and helper functions provided by a helper virus, for example AV genes E1a, E1b55K, E2a, E4orf6, and VA (Weitzman et al., Adeno-associated virus biology. Adeno-Associated Virus: Methods and Protocols, pp. 1-23, 2011). Production of AAV vector can also result in the production of helper virus particles, which must be removed or inactivated prior to use of the AAV vector. Numerous cell types are suitable for producing AAV vectors, including HEK293 cells, COS cells, HeLa cells, BHK cells, Vero cells, and A549 cells, as well as insect cells, including Sf9, Sf-21, Tn-368, and BTI-Tn-5B1-4 (High-Five) cells (See e.g. U.S. Pat. Nos. 6,156,303, 5,387,484, 5,741,683, 5,691,176, 5,688,676, 8,163,543, U.S. Publication No. 20020081721, PCT Publication Nos. WO00/47757, WO00/24916, and WO96/17947). AAV vectors are typically produced in these cell types by one plasmid containing the ITR-flanked expression cassette, and one or more additional plasmids providing the additional AAV and helper virus genes.

AAV of any serotype may be used in the present invention. Similarly, it is contemplated that any AV type may be used, and a person of skill in the art will be able to identify AAV and AV types suitable for the production of their desired recombinant AAV vector (rAAV). AAV and AV particles may be purified, for example by affinity chromatography, iodixonal gradient, or CsCl gradient.

The genome of wild-type AAV is single-stranded DNA and is approximately 4.7 kb. AAV vectors may have single-stranded genomes that are 4.7 kb in size, or are larger or smaller than 4.7 kb, including oversized genomes that are as large as 5.2 kb, or as small as 3.0 kb. Further, vector genomes may be substantially self-complementary, so that within the virus the genome is substantially double stranded. AAV vectors containing genomes of all types are suitable for use in the method of the instant invention.

As discussed above, AAV requires co-infection with a helper virus in order to enter the infectious phase of its life cycle. Helper viruses include Adenovirus (AV), including recombinant AV, and herpes simplex virus (HSV), including recombinant HSV. Systems also exist for producing AAV in insect cells using baculovirus, including recombinant baculovirus. It has also been proposed that papilloma viruses may provide a helper function for AAV (see, e.g., Hermonat et al., Molecular Therapy 9, S289-S290 (2004)), and suitable papilloma viruses may be used in the methods of the instant invention. Helper viruses include any virus capable of creating an allowing AAV replication. AV is a nonenveloped nuclear DNA virus with a double-stranded DNA genome of approximately 36 kb. AV is capable of rescuing latent AAV in a cell, by providing E1a, E1b55K, E2a, E4orf6, and VA genes, allowing AAV replication and encapsidation. HSV is a family of viruses that have a relatively large double-stranded linear DNA genome encapsidated in an icosahedral capsid, which is wrapped in a lipid bilayer envelope. HSV are infectious and highly transmissible. The following HSV-1 replication proteins were identified as necessary for AAV replication: the helicase/primase complex (ULS, UL8, and UL52) and the DNA binding protein ICP8 encoded by the UL29 gene, with other proteins enhancing the helper function.

2. Production of rAAV

The present invention comprises the production of a recombinant adeno-associated virus vector (rAAV) from a host cell, using any suitable method known in the art. As used herein, the term "host cell" refers to any cell or cells capable of producing a rAAV. In some embodiments, the host cell is a mammalian cell, for example, a HeLa cell, COS cell, HEK293 cell, A549 cell, BHK cell, or Vero cell. In other embodiments, the host cell is an insect cell, for example, a Sf9 cell, Sf-21 cell, Tn-368 cell, or BTI-Tn-5B1-4 (High-Five) cell. Unless otherwise indicated, the terms "cell" or "cell line" are understood to include modified or engineered variants of the indicated cell or cell line.

As discussed above, to allow for production of rAAV, the host cell must be provided with AAV inverted terminal repeats (ITRs) (which may, for example, flank a heterologous nucleotide sequence of interest), AAV rep and cap gene functions, as well as additional helper functions. These may be provided to the host cell using a variety of appropriate plasmids or vectors. Additional helper functions can be provided by, for example, an adenovirus (AV) infection, by a plasmid that carries all of the required AV helper function genes, or by other viruses such as HSV or baculovirus. Any genes, gene functions, or other genetic material necessary for rAAV production by the host cell may transiently exist within the host cell, or be stably inserted into the host cell genome. In some embodiments, the host cell is a producer cell comprising AAV rep and cap gene functions and a rAAV vector genome. In some embodiments, the host cell is a packaging cell comprising AAV rep and cap gene functions, which at the time of production is provided a rAAV vector genome by a separate recombinant virus. rAAV production methods suitable for use with the methods of the current invention include those disclosed in Clark et al., Human Gene Therapy 6:1329-1341 (1995), Martin et al., Human Gene Therapy Methods 24:253-269 (2013), Thorne et al., Human Gene Therapy 20:707-714 (2009), Fraser Wright, Human Gene Therapy 20:698-706 (2009), and Virag et al., Human Gene Therapy 20:807-817 (2009).

3. Tonicifying Agents

It is contemplated that any cell culture medium appropriate for propagation of the host cell may be used in the instant invention. Exemplary suitable cell culture media include minimum essential medium (MEM) such as Eagle's culture medium, Dulbecco's modified Eagle's medium (DMEM), minimum essential medium alpha (MEM-alpha), mesenchymal cell basal medium (MSCBM), Ham's F-12 medium and Ham's F-10 medium, DMEM/F12 medium, William's medium E, RPMI-1640 medium, MCDB medium, medium 199, Fisher's medium, Iscove's modified Dulbecco's medium (IMDM), Leibovitz's L-15 medium, and McCoy's modified medium.

Osmolality is a measure of the number of dissolved particles per kilogram of solvent. The osmolality of a solution can be measure by freezing point depression or vapor pressure depression. A tonicifying agent is any agent capable of increasing the osmolality of a solution without substantially adversely affecting other important attributes of the solution. Appropriate tonicifying agents will thus vary depending on the nature and purpose of the solution. In the case of cell culture media, an appropriate tonicifying agent is one that is non-toxic, and will not substantially alter the pH, buffering capacity, and nutrient density of the media. Ionic tonicifying agents are those that dissociate into ions, for example, salts such as NaCl, KCl, $NaNO_3$, $NaHCO_3$, $Na_2SO_4$, $Na_2HPO_4$, $NaH_2PO_4$, $NaNO_3$, $KNO_3$, $K_2SO_4$, $K_2HPO_4$, $KH_2PO_4$, and $KNO_3$. Non-ionic tonicifying agents are those that do not dissociate into ions, for example, sugars such as sucrose, fructose, glucose, galactose, mannose, maltose, and trehalose.

In some embodiments of the current invention, host cells are cultured in suspension culture. During suspension culture, metabolically active cells will acidify the cell culture medium in which they are grown, and the pH of the culture medium must be periodically adjusted via the addition of sterile $Na_2CO_3$ or NaOH to return the pH to optimal levels. It will be apparent the addition of $Na_2CO_3$ or NaOH, as well as the metabolic activity of the cells in culture will increase the osmolality of the culture media. For this reason, the increased osmolality of the instant invention is the lowest osmolality to which the cells are exposed, and the osmolality increases over the duration of culture.

4. Purification of rAAV Particles

In some embodiments of the current invention, the rAAV particles are harvested and/or purified from the host cell that has been incubated in cell culture media containing one or more tonicifying agents and having an osmolality of 360 mOsm/kg or higher at the start of the incubation period. rAAV particles may be obtained from host cells by lysing the cells. Lysis of host cells can be accomplished by methods that chemically or enzymatically treat the cells in order to release infections viral particles. These methods include the use of nucleases such as benzonase or DNAse, proteases such as trypsin, or detergents or surfactants. Physical disruption, such as homogenization or grinding, or the application of pressure via a microfluidizer pressure cell, or freeze-thaw cycles may also be used. Alternatively, supernatant may be collected from host cells without the need for cell lysis. As used herein, "total rAAV" refers to the total rAAV produced by a host cell, and "secreted rAAV" or "extracellular rAAV" refers to rAAV that can be can be harvested from a host cell without a cell lysis step.

After harvesting rAAV particles, it may be necessary to purify the sample containing rAAV to remove, for example, the cellular debris resulting from cell lysis. Methods of minimal purification of AAV particles are known in the art. Two exemplary purification methods are Cesium chloride (CsCl)- and iodixanol-based density gradient purification. Both methods are described in Strobel et al., Human Gene Therapy Methods., 26(4): 147-157 (2015). Minimal purification can also be accomplished using affinity chromatography using, for example AVB Sepharose affinity resin (GE Healthcare Bio-Sciences AB, Uppsala, Sweden). Methods of AAV purification using AVB Sepharose affinity resin are described in, for example, Wang et al., Mol Ther Methods Clin Dev., 2:15040 (2015). Following purification, rAAV particles may be filtered and stored at ≤−60° C.

5. Quantification of rAAV Particles

Quantification of rAAV particles is complicated by the fact that AAV infection does not result in cytopathic effect in vitro, and therefore plaque assays cannot be used to determine infectious titers. rAAV particles can be quantified using a number of methods, however, including quantitative polymerase chain reaction (qPCR) (Clark et al., Hum. Gene Ther. 10, 1031-1039 (1999)) or dot-blot hybridization (Samulski et al., J. Virol. 63, 3822-3828 (1989)), or by optical density of highly purified vector preparations (Sommer et al., Mol. Ther. 7, 122-128 (2003)). DNase-resistant particles (DRP) can be quantified by real-time quantitative polymerase chain reaction (qPCR) (DRP-qPCR) in a thermocycler (for example, an iCycler iQ 96-well block format thermocycler (Bio-Rad, Hercules, Calif.)). In this technique, samples containing rAAV particles are incubated in the presence of DNase I (100 U/ml; Promega, Madison, Wis.) at 37° C. for 60 min, followed by proteinase K (Invitrogen, Carlsbad, Calif.) digestion (10 U/ml) at 50° C. for 60 min, and then denatured at 95° C. for 30 min. The primer-probe set used should be specific to a non-native portion of the rAAV vector genome, for example, the poly(A) sequence of the protein of interest. The PCR product can be amplified using any appropriate set of cycling parameters, based on the length and composition of the primers, probe, and amplified sequence. Alternative protocols are disclosed in, for example, Lock et al., Human Gene Therapy Methods 25(2): 115-125 (2014).

The infectivity of rAAV particles can be determined using a TCID50 (tissue culture infectious dose at 50%) assay, as described for example in Zhen et al., Human Gene Therapy 15:709-715 (2004). In this assay, rAAV vector particles are serially diluted and used to co-infect a Rep/Cap-expressing cell line along with AV particles in 96-well plates. 48 hours post-infection, total cellular DNA from infected and control wells is extracted. rAAV vector replication is then measured using qPCR with transgene-specific probe and primers. TCID50 infectivity per milliliter (TCID50/ml) is calculated with the Karber equation, using the ratios of wells positive for AAV at 10-fold serial dilutions.

Throughout the description, where apparatus, devices, and systems are described as having, including, or comprising specific components, or where processes and methods are described as having, including, or comprising specific steps, it is contemplated that, additionally, there are apparatus, devices, and systems of the present invention that consist essentially of, or consist of, the recited components, and that there are processes and methods according to the present invention that consist essentially of, or consist of, the recited processing steps.

Practice of the invention will be more fully understood from the foregoing examples, which are presented herein for illustrative purposes only, and should not be construed as limiting the invention in any way.

EXAMPLES

Example 1

A HeLa producer cell line derived from the HeLa S3 parental cell line was used to produce rAAV in this experiment. In this system, a single plasmid containing three components: the vector sequence, the AAV rep and cap genes and a selectable marker gene was transfected into HeLa S3 cells, and a stable integrant was selected. The cells were cultured in protein free, chemically defined cell culture medium with a 10% fraction of culture medium carried over through inoculation. Culture media were supplemented with NaCl to a final osmolality either 266, 342, or 370 mOsmo/Kg in 250 mL shake flasks with a starting volume of 100 mL and an initial cell density of $1\times10^6$ cells/mL. Cells were maintained at 37° C. and 5% $CO_2$ for 4 days with 10% fraction of feed for all conditions. The cultures were sampled daily to monitor cell growth and metabolites and the pH was adjusted equally across flasks as needed using 1M $Na_2CO_3$. At the end of 4 days in culture, total and extracellular yield of rAAV and Ad5 was determined.

Extracellular yield was determined by removing samples of cell culture media containing suspended cells from each shake flask at the end of 4 days, filtering with 0.2 μm PES (polyethersulfone) syringe filter and quantifying the rAAV and Ad5 genomes in each sample using quantitative real-time PCR.

Total yield was determined by removing samples of cell culture media containing suspended cells from each shake flask at the end of 4 days, lysing cells with detergent, filtering with 0.2 μm PES (polyethersulfone) syringe filter, and quantifying the rAAV and Ad5 genomes in each sample using quantitative real-time PCR.

Figure 1A:
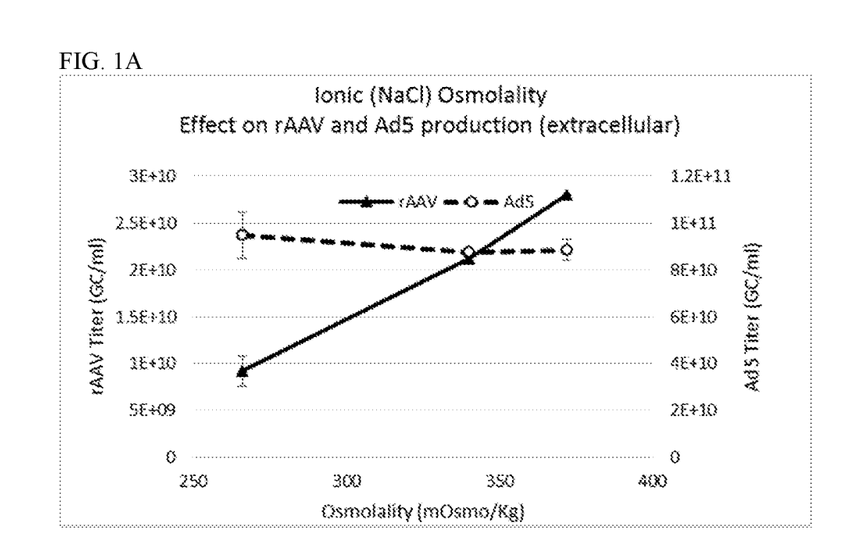
FIG. 1A depicts the effect of the addition of the ionic tonicifying agent NaCl on the production of extracellular rAAV and Ad5 in a HeLa producer cell line at 4 days post inoculation and infection. rAAV and Ad5 production was quantified by qPCR. Each value represents the mean of two independent experiments.
Figure 1B:
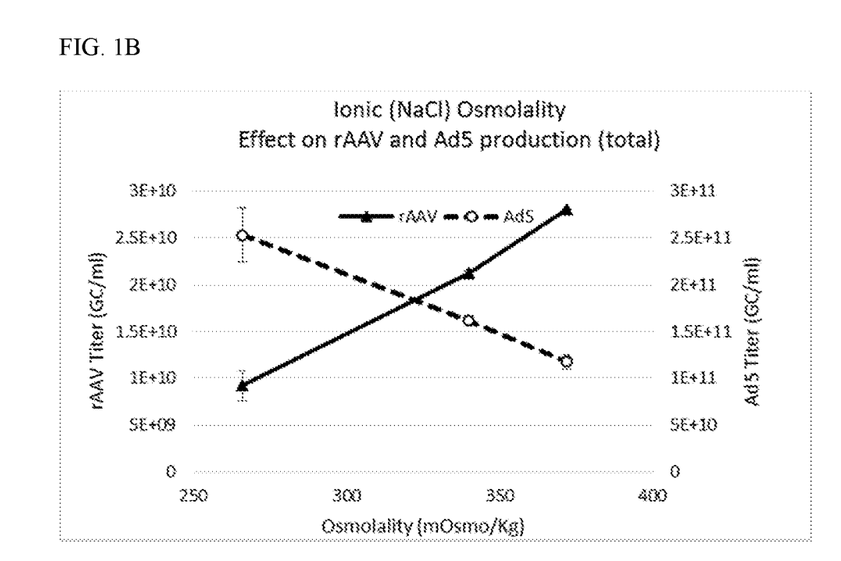
FIG. 1B depicts the effect of the addition of the ionic tonicifying agent NaCl on the production of total rAAV and Ad5 in a HeLa producer cell line at 4 days post inoculation and infection. rAAV and Ad5 production was quantified by qPCR. Each value represents the mean of two independent experiments.

Results of this experiment are presented in FIGS. 1A and 1B. As depicted in FIG. 1A, increasing the osmolality of culture media by adding an ionic tonicifying agent, NaCl, resulted in an increase in the production of extracellular rAAV, with no significant change in the production of extracellular Ad5. As depicted in FIG. 1B, increasing the osmolality of culture media by adding an ionic tonicifying agent, NaCl, resulted in an increase in the production of total rAAV, together with a decrease in production of total Ad5.

Example 2

Cells were cultured as described in Example 1, with the exception that media were supplemented with the non-ionic tonicifying agent sucrose to a final osmolality of 266, 286, 305, 353 or 390 mOsmo/Kg and no additional NaCl was added.

Figure 2A:
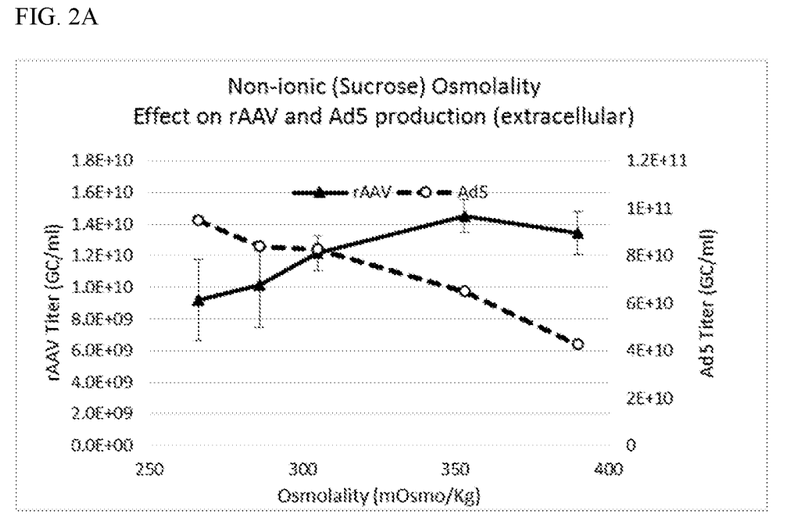
FIG. 2A depicts the effect of the addition of the non-ionic tonicifying agent sucrose on the production of extracellular rAAV and Ad5 in a HeLa producer cell line at 4 days post inoculation and infection. rAAV and Ad5 production was quantified by qPCR. Each value represents the mean of two independent experiments.
Figure 2B:
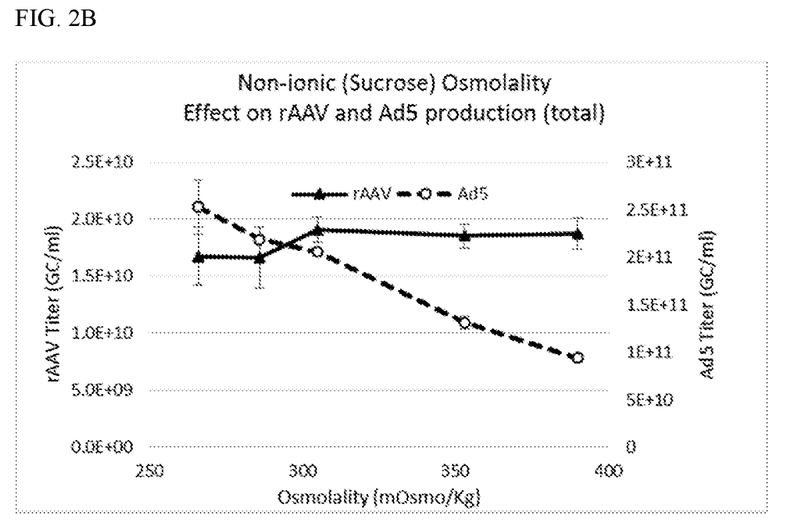
FIG. 2B depicts the effect of the addition of the non-ionic tonicifying agent sucrose on the production of total rAAV and Ad5 in a HeLa producer cell line at 4 days post inoculation and infection. rAAV and Ad5 production was quantified by qPCR. Each value represents the mean of two independent experiments.

Results from this experiment are presented in FIGS. 2A and 2B. As depicted in FIG. 2A, increasing the osmolality of culture media by adding a non-ionic tonicifying agent, sucrose, resulted in an increase in extracellular rAAV production and a decrease in extracellular Ad5 production. As depicted in FIG. 2B, increasing the osmolality of culture media by adding a non-ionic tonicifying agent, sucrose, resulted in no change in total rAAV production and a decrease in total Ad5 production.

Numbered Embodiments

1. A method for producing a recombinant adeno-associated virus vector (rAAV) using a helper virus, the method comprising incubating a host cell capable of producing rAAV in the presence of helper virus for an incubation period in a cell culture medium containing helper virus and one or more tonicifying agents and having an osmolality of 360 mOsm/kg or higher at the start of the incubation period.

2. The method of claim 1, wherein the host cell is also capable of producing helper virus.

3. The method of any preceding claim, wherein the host cell comprises a genome, said genome comprising one or more AAV genes stably integrated therein.

4. The method of any preceding claim, wherein the cell culture medium has an osmolality of 375 mOsm/kg or higher at the start of the incubation period.

5. The method of any preceding claim, wherein the cell culture medium has an osmolality of 400 mOsm/kg or higher at the start of the incubation period.

6. The method of any preceding claim, wherein the cell culture medium has an osmolality at the start of the incubation period sufficient to produce a 20% reduction in total helper virus production compared to a host cell incubated in a medium with an osmolality of 266 mOsm/kg.

7. The method of any preceding claim, wherein the cell culture medium has an osmolality at the start of the incubation period sufficient to produce a 30% reduction in total helper virus production compared to a host cell incubated in a medium with an osmolality of 266 mOsm/kg.

8. The method of any preceding claim, wherein the cell culture medium has an osmolality at the start of the incubation period sufficient to produce a 40% reduction in total helper virus production compared to a host cell incubated in a medium with an osmolality of 266 mOsm/kg.

9. The method of any preceding claim, wherein the cell culture medium has an osmolality at the start of the incubation period sufficient to produce a 50% reduction in total helper virus production compared to a host cell incubated in a medium with an osmolality of 266 mOsm/kg.

10. The method of any preceding claim, wherein the cell culture medium has an osmolality at the start of the incubation period sufficient to produce at least a 50% increase in total rAAV production compared to a host cell incubated in a medium with an osmolality of 266 mOsm/kg.

11. The method of any preceding claim, wherein the cell culture medium has an osmolality at the start of the incubation period sufficient to produce at least a 100% increase in total rAAV production compared to a host cell incubated in a medium with an osmolality of 266 mOsm/kg.

12. The method of any preceding claim, wherein the cell culture medium has an osmolality at the start of the incubation period sufficient to produce at least a 150% increase in total rAAV production compared to a host cell incubated in a medium with an osmolality of 266 mOsm/kg.

13. The method of any preceding claim, wherein the cell culture medium has an osmolality at the start of the incubation period sufficient to produce at least a 200% increase in total rAAV production compared to a host cell incubated in a medium with an osmolality of 266 mOsm/kg.

14. The method of any preceding claim, wherein at least one tonicifying agent is an ionic tonicifying agent.

15. The method of any preceding claim, wherein at least one tonicifying agent is selected from the group comprising: NaCl, KCl, $NaNO_3$, $NaHCO_3$, $Na_2SO_4$, $Na_2HPO_4$, $NaH_2PO_4$, $NaNO_3$, $KNO_3$, $K_2SO_4$, $K_2HPO_4$, $KH_2PO_4$, and $KNO_3$.

16. The method of claim 15, wherein one tonicifying agent is NaCl.

17. The method of claim 16, wherein at the start of the incubation period the concentration of NaCl in the cell culture medium is 4.5 g/L or higher.

18. The method of claim 16, wherein at the start of the incubation period the concentration of NaCl in the cell culture medium is 6.5 g/L or higher.

19. The method of claim 16, wherein at the start of the incubation period the concentration of NaCl in the cell culture medium is 7 g/L or higher.

20. The method of claim 16, wherein at the start of the incubation period the concentration of NaCl in the cell culture medium is 7.5 g/L or higher.

21. The method of any one of claims 14-20, wherein at the start of the incubation period the cell culture medium contains an ionic tonicifying agent at a concentration sufficient to produce at least a 50% increase in total rAAV production and a 20% decrease in helper virus production compared to a host cell incubated in a medium with an osmolality of 266 mOsm/kg.

22. The method of claim 21, wherein at the start of the incubation period the cell culture medium contains an ionic tonicifying agent at a concentration sufficient to produce at least a 100% increase in total rAAV production and a 30% decrease in helper virus production compared to a host cell incubated in a medium with an osmolality of 266 mOsm/kg.

23. The method of claim 22, wherein at the start of the incubation period the cell culture medium contains an ionic tonicifying agent at a concentration sufficient to produce at least a 150% increase in total rAAV production and a 40% decrease in helper virus production compared to a host cell incubated in a medium with an osmolality of 266 mOsm/kg.

24. The method of claim 23, wherein at the start of the incubation period the cell culture medium contains an ionic tonicifying agent at a concentration sufficient to produce at least a 200% increase in total rAAV production and a 50% decrease in helper virus production compared to a host cell incubated in a medium with an osmolality of 266 mOsm/kg.

25. The method of any one of claims 1-13, wherein the tonicifying agent is a non-ionic tonicifying agent.

26. The method of claim 25, wherein the tonicifying agent is a sugar.

27. The method of claim 26, wherein the tonicifying agent is a disaccharide.

28. The method of claim 26, wherein the tonicifying agent is selected from the group consisting of sucrose, fructose, glucose, galactose, mannose, maltose, and trehalose.

29. Then method of claim 28, wherein the tonicifying agent is sucrose.

30. The method of claim 29, wherein at the start of the incubation period the concentration of sucrose in the cell culture medium is 6.8 g/L or higher.

31. The method of claim 29, wherein at the start of the incubation period the concentration of sucrose in the cell culture medium is 13.7 g/L or higher.

32. The method of claim 29, wherein at the start of the incubation period the concentration of sucrose in the cell culture medium is 29.4 g/L or higher.

33. The method of claim 29, wherein at the start of the incubation period the concentration of sucrose in the cell culture medium is 41.1 g/L or higher.

34. The method of any preceding claim, wherein the cell culture medium is a serum-free cell culture medium.

35. The method of any preceding claim, wherein the cell culture medium is a protein-free cell culture medium.

36. The method of any preceding claim, wherein the cell culture medium is selected from the group consisting of MEM, DMEM, RPMI, Ham's F-12 medium, Leibovitz's L-15 medium, and mixtures thereof, said medium being supplemented with one or more tonicifying agents.

37. The method of any preceding claim, wherein the cell culture medium consists essentially of DMEM supplemented with one or more tonicifying agents.

38. The method of any preceding claim, wherein the host cell is a mammalian cell.

39. The method of any preceding claim, wherein the host cell is selected from the group consisting of HeLa, HEK293, COS, A549, BHK, and Vero cells.

40. The method of claim 39, wherein the host cell is a HeLa cell.

41. The method of any one of claims 1-37, wherein the host cell is an insect cell.

42. The method of claim 41 wherein the host cell is selected from the group consisting of Sf9, Sf-21, Tn-368, and BTI-Tn-5B1-4 (High-Five) cells.

43. The method of any preceding claim, wherein the helper virus is selected from the group consisting of adenovirus, herpes virus, baculovirus, and recombinant forms of any of the foregoing viruses.

44. The method of any one of claims 1 to 40, wherein the helper virus is an adenovirus (AV).

45. The method of claim 44 wherein the helper virus is Ad5.

46. The method of any preceding claim, wherein the host cell comprises a heterologous nucleotide sequence flanked by AAV inverted terminal repeats.

47. The method of any preceding claim, wherein the host cell comprises rep and cap genes.

48. The method of any preceding claim, wherein the host cell comprises helper virus genes.

49. The method of any preceding claim, wherein the host cell comprises a heterologous nucleotide sequence flanked by AAV inverted terminal repeats, rep and cap genes, and helper virus genes.

50. The method of any preceding claim, wherein the host cell is incubated in the cell culture medium for a period of at least 2 days.

51. The method of claim 50, wherein the incubation period is at least 3 days.

52. The method of claim 51, wherein the incubation period is about 4 days.

53. The method of any preceding claim, further comprising the steps of harvesting and purifying the rAAV.

54. A cell culture system comprising:
 a. a host cell capable of producing rAAV;
 b. a helper virus; and
 c. a cell culture medium with an osmolality of 360 mOsm/kg or higher when measured immediately after the host cell is introduced into the cell culture medium.

55. The cell culture system of claim 54, wherein the cell culture medium has an osmolality of 375 mOsm/kg or higher.

56. The cell culture system of claim 55, wherein the cell culture medium has an osmolality of 400 mOsm/kg or higher.

57. The cell culture system of any one of claims 54-56, wherein the cell culture medium has an osmolality sufficient to produce a 20% reduction in total helper virus production compared to a host cell incubated in a medium with an osmolality of 266 mOsm/kg.

58. The cell culture system of any one of claims 54-56, wherein the cell culture medium has an osmolality sufficient to produce a 30% reduction in total helper virus production compared to a host cell incubated in a medium with an osmolality of 266 mOsm/kg.

59. The cell culture system of any one of claims 54-56, wherein the cell culture medium has an osmolality sufficient to produce a 40% reduction in total helper virus production compared to a host cell incubated in a medium with an osmolality of 266 mOsm/kg.

60. The cell culture system of any one of claims 54-56, wherein the cell culture medium has an osmolality sufficient to produce a 50% reduction in total helper virus production compared to a host cell incubated in a medium with an osmolality of 266 mOsm/kg.

61. The cell culture system of any one of claims 54-56, wherein the cell culture medium has an osmolality sufficient to produce at least a 50% increase in total rAAV production compared to a host cell incubated in a medium with an osmolality of 266 mOsm/kg.

62. The cell culture system of any one of claims 54-56, wherein the cell culture medium has an osmolality sufficient to produce at least a 100% increase in total rAAV production compared to a host cell incubated in a medium with an osmolality of 266 mOsm/kg.

63. The cell culture system of any one of claims 54-56, wherein the cell culture medium has an osmolality sufficient to produce at least a 150% increase in total rAAV production compared to a host cell incubated in a medium with an osmolality of 266 mOsm/kg.

64. The cell culture system of any one of claims 54-56, wherein the cell culture medium has an osmolality sufficient to produce at least a 200% increase in total rAAV production compared to a host cell incubated in a medium with an osmolality of 266 mOsm/kg.

65. The cell culture system of any one of claims 54-64, wherein at least one tonicifying agent is an ionic tonicifying agent.

66. T The cell culture system of any one of claims 54-64, wherein at least one tonicifying agent is selected from the group comprising: NaCl, KCl, NaNO$_3$, Na$_2$SO$_4$, Na$_2$HPO$_4$, NaH$_2$PO$_4$, NaNO$_3$, KNO$_3$, K$_2$SO$_4$, K$_2$HPO$_4$, KH$_2$PO$_4$, and KNO$_3$.

67. The cell culture system of any one of claims 54-64, wherein one tonicifying agent is NaCl.

68. The cell culture system of claim 67, wherein the concentration of NaCl in the cell culture medium is 4.5 g/L or higher.

69. The cell culture system of claim 67, wherein the concentration of NaCl in the cell culture medium is 6.5 g/L or higher.

70. The cell culture system of claim 67, wherein the concentration of NaCl in the cell culture medium is 7 g/L or higher.

71. The cell culture system of claim 67, wherein the concentration of NaCl in the cell culture medium is 7.5 g/L or higher.

72. The cell culture system of any one of claims 54-71, wherein the cell culture medium contains an ionic tonicifying agent at a concentration sufficient to produce at least a 50% increase in total rAAV production and a 20% decrease in helper virus production compared to a host cell incubated in a medium with an osmolality of 266 mOsm/kg.

73. The cell culture system of claim 72, wherein the cell culture medium contains an ionic tonicifying agent at a concentration sufficient to produce at least a 100% increase in total rAAV production and a 30% decrease in helper virus production compared to a host cell incubated in a medium with an osmolality of 266 mOsm/kg.

74. The cell culture system of claim 72, wherein the cell culture medium contains an ionic tonicifying agent at a concentration sufficient to produce at least a 150% increase in total rAAV production and a 40% decrease in helper virus production compared to a host cell incubated in a medium with an osmolality of 266 mOsm/kg.

75. The cell culture system of claim 72, wherein the cell culture medium contains an ionic tonicifying agent at a concentration sufficient to produce at least a 200% increase in total rAAV production and a 50% decrease in helper virus production compared to a host cell incubated in a medium with an osmolality of 266 mOsm/kg.

76. The cell culture system of any one of claims 54-64, wherein the tonicifying agent is a non-ionic tonicifying agent.

77. The cell culture system of claim 76, wherein the tonicifying agent is a sugar.

78. Then cell culture system of claim 77, wherein the tonicifying agent is a disaccharide.

79. Then cell culture system of claim 78, wherein the tonicifying agent is selected from the group consisting of sucrose, fructose, glucose, galactose, mannose, maltose, and trehalose.

80. The cell culture system of claim 79, wherein the tonicifying agent is sucrose.

81. The cell culture system of claim 80, wherein the concentration of sucrose in the cell culture medium is 6.8 g/L or higher.

82. The cell culture system of claim 80, wherein the concentration of sucrose in the cell culture medium is 13.7 g/L or higher.

83. The cell culture system of claim 80, wherein the concentration of sucrose in the cell culture medium is 29.4 g/L or higher.

84. The cell culture system of claim 80, wherein the concentration of sucrose in the cell culture medium is 41.1 g/L or higher.

85. The cell culture system of any one of claims 54-84, wherein the cell culture medium is a serum-free cell culture medium.

86. The cell culture system of any one of claims 54-85, wherein the cell culture medium is a protein-free cell culture medium.

87. The cell culture system of any one of claims 54-86, wherein the cell culture medium is selected from the group consisting of MEM, DMEM, RPMI, Ham's F-12 medium, Leibovitz's L-15 medium, and mixtures thereof, said medium being supplemented with one or more tonicifying agents.

88. The cell culture system of any one of claims 54-86, wherein the cell culture medium consists essentially of DMEM supplemented with one or more tonicifying agents 89. The cell culture system of any one of claims 54-88, wherein the host cell is a mammalian cell.

90. The cell culture system of claim 89, wherein the host cell is selected from the group consisting of HeLa, HEK293, COS, A549, BHK, and Vero cells.

91. The cell culture system of claim 90, wherein the host cell is a HeLa cell.

92. The cell culture system of any one of claims 54-88, wherein the host cell is an insect cell.

93. The cell culture system of claim 92, wherein the host cell is selected from the group consisting of Sf9, Sf-21, Tn-368, and BTI-Tn-5B1-4 (High-Five) cells.

94. The cell culture system of any one of claims 54-93, wherein the helper virus is selected from the group consisting of adenovirus, herpes virus, baculovirus, and recombinant forms of any of the foregoing viruses.

95. The cell culture system of any one of claims 54-91, wherein the helper virus is an adenovirus (AV).

96. The cell culture system of claim 95 wherein the helper virus is Ad5.

97. The cell culture system of any one of claims 54-96, wherein the host cell comprises a heterologous nucleotide sequence flanked by AAV inverted terminal repeats.

98. The cell culture system of any one of claims 54-96, wherein the host cell comprises rep and cap genes.

99. The cell culture system of any one of claims 54-96, wherein the host cell comprises helper virus genes.

100. The cell culture system of any one of claims 54-96, wherein the host cell comprises a heterologous nucleotide sequence flanked by AAV inverted terminal repeats, rep and cap genes, and helper virus genes.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. An rAAV production system whose total rAAV production is increased compared to total rAAV production from a system comprising a cell culture medium having an osmolality of 266 mOsm/kg, the rAAV production system comprising:
   a) HeLa host cells capable of producing rAAV;
   b) a helper virus; and
   c) a cell culture medium having an osmolality of 360 mOsm/kg or higher when measured immediately after the HeLa host cells are introduced into the cell culture medium and throughout rAAV production, the cell culture medium comprising one or more non-ionic tonicifying agents selected from the group consisting of sucrose, fructose, glucose, galactose, mannose, maltose, and trehalose.

2. The rAAV production system of claim 1, wherein the cell culture medium has an osmolality of
   a) 375 mOsm/kg or higher; or
   b) 400 mOsm/kg or higher.

3. The rAAV production system of claim 1, wherein the cell culture medium has an osmolality sufficient to produce
   a) a 20% reduction, a 30% reduction, a 40% reduction, or a 50% reduction in total helper virus production compared to HeLa host cells cultured in a cell culture medium with an osmolality of 266 mOsm/kg; and/or
   b) at least a 50% increase, at least a 100% increase, at least a 150% increase, or at least a 200% increase in total rAAV production compared to HeLa host cells cultured in a cell culture medium with an osmolality of 266 mOsm/kg.

4. The rAAV production system of claim 1, further comprising one or more
   ionic tonicifying agents selected from the group consisting of NaCl, KCl, NaNO$_3$, Na$_2$SO$_4$, Na$_2$HPO$_4$, NaH$_2$PO$_4$, NaNO$_3$, KNO$_3$, K$_2$SO$_4$, K$_2$HPO$_4$, KH$_2$PO$_4$, and KNO$_3$.

5. The rAAV production system of claim 4, wherein the ionic tonicifying agent is NaCl.

6. The rAAV production system of claim 5, wherein the concentration of NaCl in the cell culture medium is
   a) 4.5 g/L or higher;
   b) 6.5 g/L or higher;
   c) 7 g/L or higher; or
   d) 7.5 g/L or higher.

7. The rAAV production system of claim 4, wherein the cell culture medium contains an ionic tonicifying agent at a concentration sufficient to produce
   a) at least a 50% increase in total rAAV production and a 20% decrease in helper virus production;
   b) at least a 100% increase in total rAAV production and a 30% decrease in helper virus production;
   c) at least a 150% increase in total rAAV production and a 40% decrease in helper virus production; or
   d) at least a 200% increase in total rAAV production and a 50% decrease in helper virus production compared to HeLa host cells cultured in a cell culture medium with an osmolality of 266 mOsm/kg.

8. The rAAV production system of claim 1, wherein the non-ionic tonicifying agent is sucrose.

9. The rAAV production system of claim 8, wherein the concentration of sucrose in the cell culture medium is
   a) 6.8 g/L or higher;
   b) 13.7 g/L or higher;
   c) 29.4 g/L or higher; or
   d) 41.1 g/L or higher.

10. The rAAV production system of claim 1, wherein the cell culture medium is a serum-free cell culture medium and/or protein-free cell culture medium.

11. The rAAV production system of claim 10, wherein the cell culture medium is selected from the group consisting of MEM, DMEM, RPMI, Ham's F-12 medium, Leibovitz's L-15 medium, and mixtures thereof, said medium being supplemented with the one or more tonicifying agents.

12. The rAAV production system of claim 10, wherein the cell culture medium consists essentially of DMEM supplemented with the one or more tonicifying agents.

13. The rAAV production system of claim 1, wherein the helper virus is selected from the group consisting of adenovirus (AV), herpes virus, baculovirus, and recombinant forms of any of the foregoing viruses.

14. The rAAV production system of claim 13, wherein the helper virus is an adenovirus.

15. The rAAV production system of claim 14, wherein the helper virus is Ad5.

16. The rAAV production system of claim 1, wherein the HeLa host cells comprise a heterologous nucleotide sequence flanked by AAV inverted terminal repeats, rep and cap genes, and helper virus genes.

17. The rAAV production system of claim 1, wherein the HeLa host cells comprise a genome, said genome comprising one or more AAV genes stably integrated therein.

* * * * *